United States Patent [19]

de Groot et al.

[11] Patent Number: 5,838,485
[45] Date of Patent: Nov. 17, 1998

[54] SUPERHETERODYNE INTERFEROMETER AND METHOD FOR COMPENSATING THE REFRACTIVE INDEX OF AIR USING ELECTRONIC FREQUENCY MULTIPLICATION

[75] Inventors: Peter de Groot, Middletown, Conn.; Henry A. Hill, Tucson, Ariz.

[73] Assignee: Zygo Corporation, Middlefield, Conn.

[21] Appl. No.: 700,112

[22] Filed: Aug. 20, 1996

[51] Int. Cl.⁶ .................................................. G01B 9/02
[52] U.S. Cl. ........................ 356/361; 356/358; 356/349; 356/351
[58] Field of Search .................... 356/358, 361, 356/349, 351

[56] References Cited

U.S. PATENT DOCUMENTS

| | | |
|---|---|---|
| 3,647,302 | 3/1972 | Zipla et al. . |
| 4,005,936 | 2/1977 | Redman et al. . |
| 4,688,940 | 8/1987 | Sommargren et al. ................. 356/358 |
| 4,907,886 | 3/1990 | Dandliker ............................... 356/358 |
| 4,948,254 | 8/1990 | Ishida ..................................... 356/358 |
| 5,404,222 | 4/1995 | Lis ......................................... 356/358 |
| 5,537,209 | 7/1996 | Lis ......................................... 356/358 |

OTHER PUBLICATIONS

Lis, Steven, A., "*An Air Turbulence Compensated Interferometer For IC Manufacturing*", presented at the SPIE Conference on Optical/Laser Microlithography VIII, Feb. 24, 1995, Santa Monica, California.

Zanoni, Dr. Carl A., "*Differential Interferometer Arrangements for Distance and Angle Measurements: Principles, Advantages and Applications*", VDI BERICHTE, 1989, pp. 93–106.

Ishida, Akira., "*Two–Wavelength Displacement–Measuring Interferometer Using Second–Harmonic Light to Eliminate Air–Turbulence–Induced Errors*", Japanese Journal of Applied Physics, vol. 28(3), Mar. 1989, pp. 587–589.

Zhu, Yucong, et al., "*Long–Arm Two–Color Interferometer for Measuring the Change of Air Refractive Index*", SPIE, Optics in Complex Systems, vol. 1319, 1990, pp. 538–539.

Earnshaw, K.B., et al., "*Two–Laser Optical Distance–Measuring Instrument That Corrects for the Atmospheric Index of Refraction*", Applied Optics, vol. 11, No. 4, Apr. 1972, pp. 749–754.

Hernandez, E.N., et al., "*Field Tests of a Two–Laser (4416A and 6328A) Optical Distance–Measuring Instrument Correcting for the Atmospheric Index of Refraction*", Journal of Geophysical Research, vol. 77, No. 35, Dec. 10, 1972, pp. 6994–6998.

Dandliker, René., et al., "*Two–Wavelength Laser Interferometry Using Superheterodyne Detection*", Optics Letters, vol. 13, No. 5, May 1988, pp. 339–341.

Dandliker, René, et al., "*High–Accuracy Distance Measurements With Multiple–Wavelength Interferometry*", Optical Engineering, vol. 34, No. 8, Aug. 1995, pp. 2407–2412.

(List continued on next page.)

*Primary Examiner*—Frank G. Font
*Assistant Examiner*—Amanda Merlino
*Attorney, Agent, or Firm*—Francis J. Caufield

[57] ABSTRACT

A method and apparatus for measuring fluctuations in the refractive index of a gas, such as air, in a measurement path (66) may be used to measure displacement of an object (67) independent of these fluctuations. A coherent source of light (1,4) provides two source light beams (11, 12) having source wavelengths ($\lambda_1, \lambda_2$) along the measurement path (66) which are substantially harmonically related to each other. The beams (11, 12) are electronically processed (98, 981, 982, 983, 984, 985) to provide modified heterodyne phase shifts based on the provided source wavelengths which are similarly harmonically related to the harmonically related source wavelengths for providing a superheterodyne modulation phase substantially insensitive to motion along the measurement path (66).

30 Claims, 3 Drawing Sheets

OTHER PUBLICATIONS

Sodnik, Zoran, et al., "*Two–Wavelength Double Heterodyne Interferometry Using A Matched Grating Technique*", Applied Optics, vol. 30, No. 22, Aug. 1, 1991, pp. 3139–3144.

Manhart, S., et al., "*Diode Laser and Fiber Optics for Dual–Wavelength Heterodyne Interferometry*", SPIE, Optics in Complex Systems, vol. 1319, 1990, pp. 214–216.

Jones, Frank E., "*The Refractivity of Air*", Journal of Research of the National Bureau of Standards, vol. 86, No. 1, Jan.–Feb. 1981, pp. 27–32.

Estler, W. Tyler, "*High–Accuracy Displacement Interferometry in Air*", Applied Optics, vol. 24, No. 6, Mar. 15, 1985, pp. 808–815.

Berg, Eduard, et al., "*Distance Corrections for Single–and Dual–Color Lasers by Ray Tracing*", Journal of Geophysical Research, vol. 85, No. B11, Nov. 10, 1980, pp. 6513–6520.

Slater, L.E., et al., "*A Multiwavelength Distance–Measuring Instrument for Geophysical Experiments*", Journal of Geophysical Research, vol. 81, No. 35, Dec. 10, 1976, pp. 6299–6306.

Erickson, Kent E., "*Long–Path Interferometry Through an Uncontrolled Atmosphere*", Journal of the Optical Society of America, vol. 52, No. 7, Jul. 1962, pp. 781–787.

Bender, Peter L., et al., "*Correction of Optical Distance Measurements for the Fluctuating Atmospheric Index of Refraction*", Journal of Geophysical Research, vol. 70, No. 10, May 15, 1965, pp. 2461–2462.

Terrien, J., "*An Air Refractometer For Interference Length Metrology*", Bureau International des Poids et Mesures, France, vol. 1, No. 3, Mar. 1965, pp. 80–83.

Matsumoto, Hirokazu, et al., "*Effects of the Atmospheric Phase Fluctuation on Long–Distance Measurement*", Applied Optics, vol. 23, No. 19, Oct. 1, 1984, pp. 3388–3394.

Gibson, George N., et al., "*Optical Path Length Fluctuations In the Atmosphere,*" Applied Optics, vol. 23, No. 23, Dec. 1, 1984, pp. 4383–4389.

Bobroff, Norman, "*Residual Errors in Laser Interferometry From Air Turbulence and Nonlinearity*", Applied Optics, vol. 26, No. 13, Jul. 1, 1987, pp. 2676–2682.

Bobroff, Norman, "*Recent Advances in Displacement Measuring Interferometry*", Measurement Science & Technology, vol. 4, No. 9, Sep. 1993, pp. 907–926.

SUPERHETERODYNE INTERFEROMETER AND METHOD FOR COMPENSATING THE REFRACTIVE INDEX OF AIR USING ELECTRONIC FREQUENCY MULTIPLICATION

CROSS REFERENCE TO RELATED APPLICATION

This application is related to the contemporaneously filed, commonly owned, copending U.S. patent application Ser. No. 08/700,113 by H. A. Hill and P. de Groot entitled "Superheterodyne Method and Apparatus for Measuring the Refractive Index of Air Using Multiple-Pass Interferometry", the contents of which are specifically incorporated by reference herein in their entirety.

FIELD OF THE INVENTION

The present invention relates to optical instruments for measuring distance and refractive index. The invention relates in particular to interferometric distance measurement independent of fluctuations in the refractive index of a gas in a measurement path.

BACKGROUND AND PRIOR ART

A frequently-encountered problem in metrology is the measurement of the refractive index of a column of air. Several techniques exist for measuring the refractive index of air under highly controlled circumstances, such as when the air column is contained in a sample cell and is monitored for temperature, pressure and physical dimension. See for example, an article entitled "An air refractometer for interference length metrology," by J. Terrien, Metrologia 1(3), 80–83 (1965).

Perhaps the most difficult measurement related to the refractive index of air is the measurement of index fluctuations over a measurement path of unknown or variable length, with uncontrolled temperature and pressure. Such circumstances arise frequently in geophysical and meteorological surveying, for which the atmosphere is obviously uncontrolled and the refractive index of air is changing dramatically because of variations in air density and composition. This problem is discussed in an article entitled "Effects of the atmospheric phase fluctuation on long-distance measurement," by H. Matsumoto and K. Tsukahara, Appl. Opt. 23(19), 3388–3394 (1984), and in an article entitled "Optical path length fluctuation in the atmosphere," by G. N. Gibson et al., Appl. Opt. 23(23), 4383–4389 (1984).

Another example of the problem encountered in measuring the refractive index of air is high-precision distance measuring interferometry, such as is employed in the microlithographic fabrication of integrated circuits. See for example an article entitled "Residual errors in laser interferometry from air turbulence and non-linearity," by N. Bobroff, Appl. Opt. 26(13), 2676–2682 (1987), and an article entitled "Recent advances in displacement measuring interferometry," also by N. Bobroff, Measurement science & tech. 4(9), 907–926 (1993). Typically the correction for fluctuations in the refractive index of air is on the order of 0.1 ppm (parts per million) in magnitude, and must be accurate to 0.005 ppm. These high levels of precision involve frequency-stabilized laser sources and high-resolution phase detection.

There are frequent references in the prior art to heterodyne methods of phase estimation, in which the phase varies with time in a controlled way. For example, in a known form of prior-art heterodyne distance-measuring interferometer, the source emits two orthogonal polarizations having slightly different optical frequencies (e.g. 2 MHz). The interferometric receiver in this case is typically comprised of a linear polarizer and a photodetector to measure the time-varying interference signal. The signal oscillates at the beat frequency, and the phase of the signal corresponds to the relative phase difference. A further representative example of the prior art in heterodyne distance-measuring interferometry is disclosed in commonly-owned U.S. Pat. No. 4,688,940 to G. E. Sommargren and M. Schaham (1987). However, these known forms of interferometric metrology are limited by fluctuations in refractive index, and, by themselves, are unsuited to the next generation of microlithography instruments.

Another known form of interferometer for distance measurement is disclosed in U.S. Pat. No. 4,005,936 entitled "Interferometric methods and apparatus for measuring distance to a surface" to J. D. Redman and M. R. Wall (1977). The prior art method taught by Redman and Wall consists of employing laser beams of two different wavelengths, each of which is split into two parts. Frequency shifts are introduced into one part of the respective beams. One part of each beam reflects from an object and recombines with the other part on a photodetector to produce an interference signal. From this interference signal a difference frequency is derived whose phase is a measure of the distance to the surface. The equivalent wavelength of the phase associated with the difference frequency is equal to the product of the two laser wavelengths divided by the difference of the two wavelengths. This prior art two-wavelength technique of Redman and Wall reduces measurement ambiguities, but is at least as sensitive to the deleterious effects of index fluctuations of the air as prior art single-wavelength techniques.

Another example of a prior art two-wavelength interferometer similar to that of Redman and Wall is disclosed in U.S. Pat. No. 4,907,886 entitled "Method and apparatus for two-wavelength interferometry with optical heterodyne processes and use for position or range finding," to R. Dändliker and W. Heerburgg. This prior art system is also described in an article entitled "Two-wavelength laser interferometry using superheterodyne detection," by entitled "R. Dändliker", R. Thalmann, and D. Prongué, Opt. Let. 13(5), 339–341 (1988) and in an article entitled "High-accuracy distance measurements with multiple-wavelength interferometry," by R. Dändliker, K. Hug, J. Politch and E. Zimmermann. The system of Dändliker et al., as taught in U.S. Pat. No. 4,907,886 employs laser beams of two wavelengths, with each of these beams comprising two polarization components separated in frequency by means of acousto-optic modulation. After passing these beams collinearly through a Michelson interferometer, the polarization components are mixed, resulting in a heterodyne signal. Since the heterodyne signal has a different frequency for each of the two wavelengths, a so-called super-heterodyne signal results therefrom, having a frequency equal to the difference in the heterodyne frequencies, and a phase associated with an equivalent wavelength equal to the product of the two laser wavelengths divided by the difference of the two wavelengths. According to U.S. Pat. No. 4,907,886, the phase of this super-heterodyne signal is assumed to be dependent only on the position of a measurement object and the equivalent wavelength. Therefore, this prior art system is also not designed to measure or compensate for the fluctuations in the index of air.

Further examples of the prior art two-wavelength superheterodyne technique developed by Redman and Wall and by Dändliker and Heerburgg (cited above) are found in an article entitled "Two-wavelength double heterodyne interferometry using a matched grating technique," by Z. Sodnik, E. Fischer, T. Ittner and H. J. Tiziani, Appl. Opt. 30(22), 3139–3144 (1991) and in an article entitled "Diode laser and fiber optics for dual-wavelength heterodyne interferometry," by S. Manhart and R. Maurer, SPIE 1319, 214–216 (1990). However, neither one of these examples addresses the problem of index fluctuations.

Thus, as illustrated by the foregoing examples, the prior art in heterodyne and superheterodyne interferometry does not provide a satisfactory method and corresponding means for measuring and compensating the fluctuation of the refractive index of air. This deficiency in the prior art results in significant measurement uncertainty, thus seriously affecting the precision of systems employing such interferometers, for example in micro-lithographic fabrication of integrated circuits. Consequently, future interferometers will necessarily have to incorporate an inventive, new method and means for measuring and compensating for refractive index fluctuations.

One known way to detect index fluctuations is to measure changes in pressure and temperature along the measurement path and calculate the effect on the refractive index of path. Mathematical equations for effecting this calculation are well known, such as disclosed in an article entitled "The refractivity of air," by F. E. Jones, J. Res. NBS 86(1), 27–32 (1981). An implementation of this prior art technique is described in an article entitled "High-accuracy displacement interferometry in air," by W. T. Estler, Appl. Opt. 24(6), 808–815 (1985). Unfortunately, this prior art technique is also unsatisfactory in that it provides only approximate values, is cumbersome, and corrects only for slow, global fluctuations in air density.

Another, more direct way to detect index fluctuations over a path is by multiple-wavelength distance measurement. The basic principle may be understood as follows. Interferometers and laser radar measure the optical path length between a reference and an object, most often in open air. The optical path length is the integrated product of the refractive index and the physical path traversed by the measurement beam. In that the refractive index varies with wavelength, but the physical path is independent of wavelength, it is generally possible to separate the physical path length from the fluctuations in refractive index, provided that the instrument employs at least two wavelengths. The variation of index with wavelength is known in the art as dispersion, therefore this technique will be referred to hereinafter as the dispersion technique.

The prior art dispersion technique for index measurement has a long history, and predates the introduction of the laser. An article entitled "Long-path interferometry through an uncontrolled atmosphere," by K. E. Erickson (J. Opt. Soc. Am. 52(7), 781–787 (1962)) describes the basic principles and provides an analysis of the feasibility of this prior art technique for geophysical measurements. Additional theoretical proposals are found in an article entitled "Correction of optical distance measurements for the fluctuating atmospheric index of refraction," by P. L. Bender and J. C. Owens (J. Geo. Res. 70(10), 2461–2462 (1965)).

Commercial distance-measuring laser radar based on this prior art dispersion technique for index compensation appeared in the 1970's. An article entitled "Two-laser optical distance-measuring instrument that corrects for the atmospheric index of refraction," by K. B. Earnshaw and E. N. Hernandez, Appl. Opt. 11(4), 749–754 (1972), discloses a prior art instrument employing microwave-modulated HeNe and HeCd lasers for operation over a 5 to 10-km measurement path. Further details of this instrument are found in an article entitled "Field Tests of a two-laser (4416A and 6328A) optical distance-measuring instrument correcting for the atmospheric index of refraction," by E. N. Hernandez and K. B. Earnshaw, J. Geo. Res. 77(35), 6994–6998 (1972). Further examples of applications of the dispersion technique are discussed in an article entitled "Distance corrections for single- and dual-color lasers by ray tracing," by E. Berg and J. A. Carter, J. Geo. Res. 85(B11), 6513–6520 (1980), and in an article entitled "A multi-wavelength distance-measuring instrument for geophysical experiments," by L. E. Slater and G. R. Huggett, J. Geo. Res. 81(35), 6299–6306 (1976).

Although prior art instrumentation for geophysical measurements typically employs intensity-modulation laser radar, it is understood in the art that optical interference phase detection is more advantageous for shorter distances. In U.S. Pat. No. 3,647,302 to R. B. Zipin and J. T. Zalusky, entitled "Apparatus for and method of obtaining precision dimensional measurements," there is disclosed a prior art interferometric displacement-measuring system employing multiple wavelengths to compensate for variations in ambient conditions such as temperature, humidity and pressure. This prior art instrument is specifically designed for operation with a movable object, that is, with a variable physical path length; however, the prior art phase-detection means of Zipin and Zalusky is insufficiently accurate for high-precision measurement.

A more modern and detailed example of a prior art technique for index measurement is the system described by Y. Zhu, H. Matsumoto, T. O'ishi in an article entitled "Long-arm two-color interferometer for measuring the change of air refractive index," SPIE 1319, Optics in complex systems, 538–539 (1990). This system employs a 1064-nm wavelength YAG laser and an 632-nm HeNe laser together with quadrature phase detection. Substantially the same prior art instrument is described in Japanese in an earlier article by Zhu et al. entitled "Measurement of atmospheric phase and intensity turbulence for long-path distance interferometer," Proc. $3^{rd}$ meeting on lightwave sensing technology, Appl Phys. Soc. of Japan, 39 (1989); however, the prior art interferometer of Zhu et al. described in these articles has insufficient resolution for all applications, such as, for example, in sub-micron prior art interferometry for microlithography.

A recent attempt at high-precision interferometry for use in microlithography is represented by the approach described in U.S. Pat. No. 4,948,254 to A. Ishida. A similar prior art device is also described by Ishida in an article entitled "Two wavelength displacement-measuring interferometer using second-harmonic light to eliminate air-turbulence-induced errors," Jpn. J. Appl. Phys. 28(3), L473–475 (1989). A displacement-measuring interferometer is disclosed in this article which eliminates errors caused by fluctuations in the refractive index by means of two-wavelength dispersion detection. An $Ar^+$ laser source provides both wavelengths simultaneously by means of a frequency-doubling crystal known in the art as BBO. The use of a BBO doubling crystal results in two wavelengths that are fundamentally phase locked, thus greatly improving the stability and accuracy of the refractive index measurement; however, the phase detection means, which employ simple homodyne quadrature detection, are insufficient for high resolution phase measurement. Further, the phase detection and signal processing means are not suitable for dynamic measurements, in which the motion of the object results in rapid variations in phase that are difficult to detect accurately.

U.S. Pat. No. 5,404,222 entitled "Interferometric measuring system with air turbulence compensation" to S. A. Lis (1995), discloses another prior art technique employing a two-wavelength interferometer and the dispersion technique for detecting and compensating index fluctuations. A similar device prior art is described by Lis in an article entitled "An air turbulence compensated interferometer for IC manufacturing," SPIE 2440 (1995). Improvement on U.S. Pat. No. 5,404,222 by S. A. Lis is disclosed in U.S. Pat. No. 5,537,209 issued July 1996. The principle innovation of this system with respect to that taught by Ishida in Jpn. J. Appl. Phys. (cited above) is the addition of another BBO doubling crystal to improve the precision of the phase detection means. The additional BBO crystal makes it possible to optically interfere two beams having wavelengths that are exactly a factor of two different. The resultant interference has a phase that is directly dependent on the index of refraction but is substantially independent of stage motion; however, the prior art system taught by Lis has the disadvantage that it is complicated and requires an additional BBO crystal for every measurement path. Since microlithography stages frequently involve six or more measurement paths, and BBO can cost more than $12,000, the use of such additional crystals are a significant cost burden. An additional disadvantage of Lis' system is that it employs a low-speed (32-Hz) phase detection system based on the physical displacement of a PZT transducer.

It is clear to applicants from the foregoing, that the prior art does not provide a practical, high-speed, high-precision method and corresponding means for measuring and compensating fluctuations in the refractive index of air. The limitations in the prior art arise principally from the following, unresolved technical difficulties: (1) prior-art heterodyne and superheterodyne interferometers are limited in accuracy by fluctuations in the refractive index of air; (2) prior-art dispersion techniques for measuring index fluctuations require extremely high accuracy in interference phase measurement, typically exceeding by an order of magnitude the typical accuracy of high-precision distance-measuring interferometers; (3) obvious modifications to prior-art interferometers to improve phase-measuring accuracy would increase the measurement time to an extent incompatible with the rapidity of stage motion in modern microlithography equipment; (4) prior-art dispersion techniques require at least two extremely stable laser sources, or a single source emitting multiple, phase-locked wavelengths; (5) prior-art dispersion techniques in microlithography applications are sensitive to stage motion during the measurement, resulting in systematic errors; and (6) prior-art dispersion techniques that employ doubling crystals such as disclosed in U.S. Pat. No. 5,404,222 to Lis as part of the detection system are expensive and complicated.

These deficiencies in the prior art which are overcome by the present invention, have lead to the absence of any practical interferometric system for performing displacement measurement for microlithography in the presence of index fluctuations.

SUMMARY OF THE INVENTION

In accordance with the present invention, an apparatus and method for measuring fluctuations in the refractive index of a gas in a measurement path, such as is useful for distance measuring interferometry independent of said fluctuations is provided which comprises: (1) a source of at least two light beams each with a different wavelength, the wavelengths having a known approximate harmonic relationship to each other or to a common reference; (2) means for introducing a frequency difference between the two orthogonal polarization states of each of the light beams, the frequency difference for each of the light beams being different for at least two beams; (3) optical means for aligning all of the light beams into a single beam so that they are substantially collinear and of substantially equal diameter along the measurement path; (4) optical means for producing phase-shifted beams by introducing phase shifts between the polarization states of each of the light beams, the magnitude of the phase shifts being proportional to the product of the physical length of the measurement path and the indices of refraction of the gas in the measurement path, the indices of refraction being a function of wavelength and different for each of said phase-shifted beams; (5) means, preferably a polarizer, for mixing the polarization components of each of the phase-shifted light beams to produce two or more mixed output beams; (6) means, preferably photoelectric detection, for producing heterodyne electrical signals from the intensity of the mixed output beams, the heterodyne electrical signals being characterized by oscillations at heterodyne frequencies related to the frequency differences between the polarization states of the light beams, the heterodyne electrical signals being further characterized by heterodyne phases; (7) means, preferably electronic, for processing the heterodyne electrical signals to generate modified heterodyne signals characterized by modified heterodyne phases that are harmonically related to the heterodyne phases; (8) means, preferably electronic, for mixing any two of the modified heterodyne electrical signals to produce at least one superheterodyne electrical signal comprised of an amplitude-modulated carrier having a superheterodyne modulation frequency equal to half the difference of the two corresponding modified heterodyne frequencies and a superheterodyne modulation phase equal to half the difference between the two corresponding modified heterodyne phases; and (9) means, preferably electronic, for analyzing the superheterodyne modulation phase for determining the fluctuations in the refractive index of the gas over the measurement path.

The principle advantages of the invention may be summarized as follows. When the source wavelengths are substantially harmonically related and the modified heterodyne phase shifts are similarly harmonically related, the present invention provides a superheterodyne modulation phase that is substantially insensitive to stage motion. The superheterodyne modulation phase is a direct measure of fluctuations in the refractive index of air. Since the superheterodyne modulation frequency may be adjusted to any convenient value, the phase-measurement accuracy for compensating index fluctuations may be appropriately enhanced. These improvements over the prior art are conveniently achieved without expensive optical components such as doubling crystals or the like, and without placing any restriction on the rapidity of stage motion.

An alternative embodiment of the invention includes the ability to compensate for unexpected fluctuations in the source wavelength, using additional monitor interferometer means and substantially the same electronic processing means as are employed in the primary apparatus. The monitor interferometer preferably comprises a fixed monitor path length having a carefully controlled refractive index, so that any measured variations in the monitor are attributable to and provide a measure of the wavelength stability.

BRIEF DESCRIPTION OF THE DRAWINGS

In the drawings, wherein like reference characters denote similar elements throughout the several views.

DETAILED DESCRIPTION OF THE INVENTION

Figure 1:
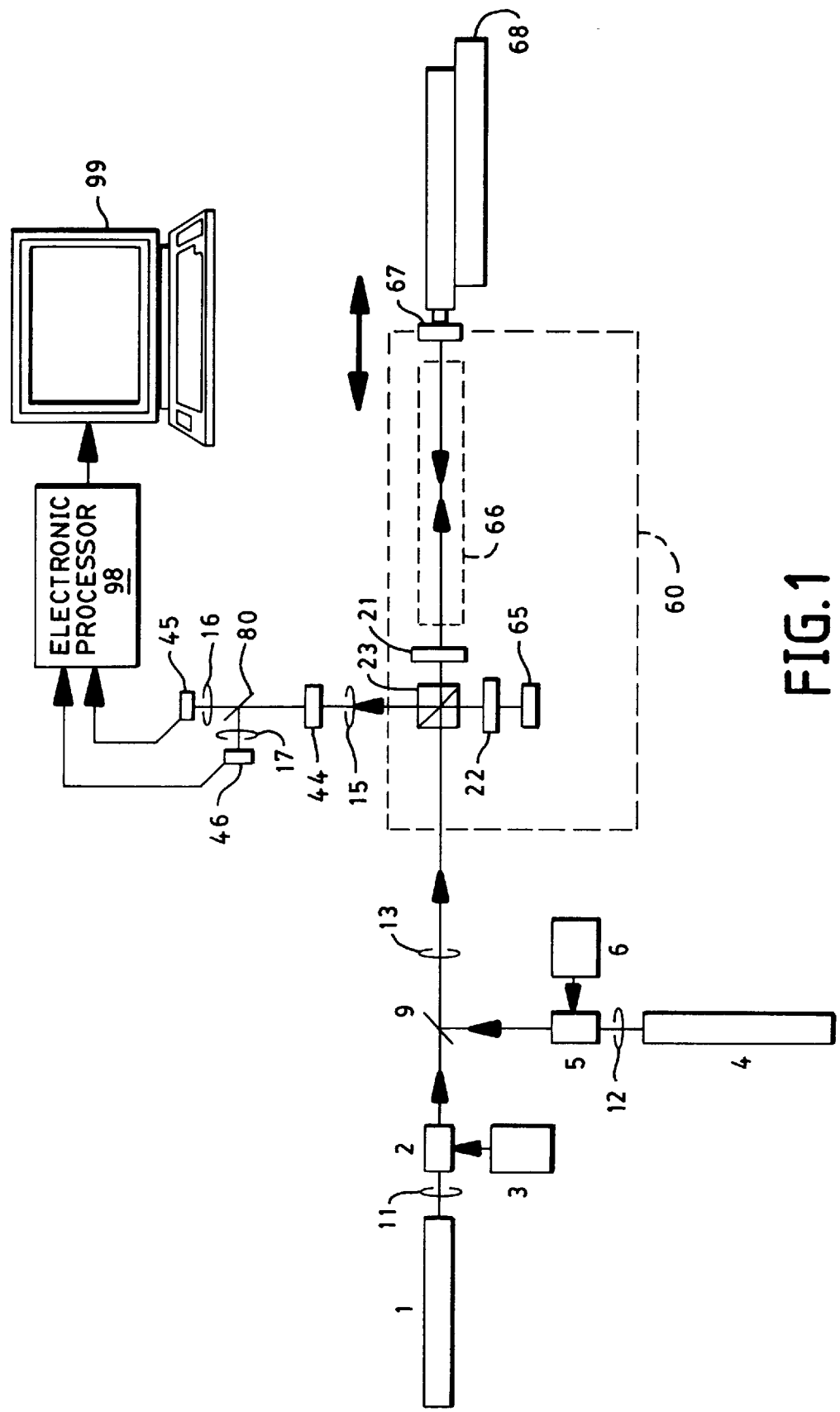
FIG. 1 is a drawing showing a preferred embodiment of the present invention.
Figure 2:
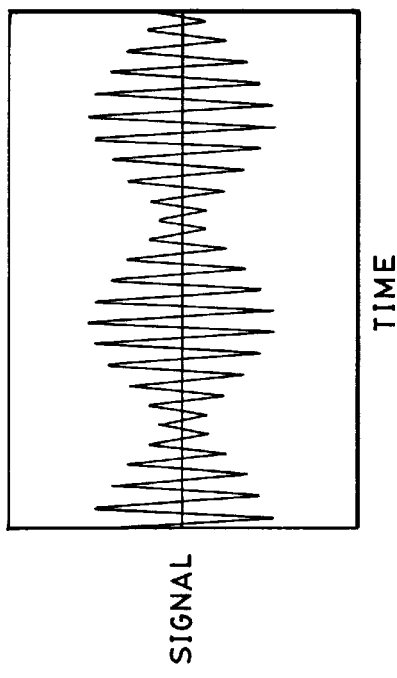
FIG. 2 is graph depicting a superheterodyne signal in accordance with the present invention.

Referring initially to FIG. 1, there is shown a presently preferred embodiment of the apparatus for the present invention measuring fluctuations in the refractive index of a gas in a measurement path 66, such as is useful for measuring the displacement of an object 67 independent of these fluctuations.

In accordance with a presently preferred method of the present invention, in a first step, a light beam 11 emitted from a source 1 passes through a modulator 2 excited by a driver 3. Source 1 is preferably a laser or like source of coherent radiation, preferably polarized, and having a wavelength $\lambda_1$. Modulator 2 may for example be an acousto-optic device or a combination of an acousto-optic device with additional optics for selectively modulating polarization components of beam 11. Modulator 2 preferably shifts the oscillation frequency of one linear polarization component of beam 11 an amount $f_1$ with respect to an orthogonal linear polarization component, with the polarization components being denoted herein as x and y, respectively. Therefore, after passing through modulator 2, polarization component x of beam 11 has an oscillation frequency shifted upwards an amount $f_1$ with respect to polarization component y of beam 11.

In a next step, a light beam 12 emitted from a source 4 passes through a modulator 5 excited by a driver 6, similar to modulator 2 and driver 3, respectively. Source 4, similarly to source 1, is preferably a laser or like source of polarized, coherent radiation, but preferably at a different wavelength, $\lambda_2$, having a known approximate harmonic relationship with respect to $\lambda_2$, such as $$p_1\lambda_2 \approx p_2\lambda_1 \text{ for } p_1, p_2 = 1,2,3,\ldots, p_1 \neq p_2$$

After passing through modulator 5, polarization component x of beam 12 has an oscillation frequency shifted upwards an amount $f_2$ with respect to polarization component y of beam 12.

It will be appreciated by those skilled in the art that beams 11 and 12 may be provided alternatively by a single laser source emitting more than one wavelength, or by a single laser source combined with optical frequency doubling means, or any equivalent source configuration capable of generating light beams of two or more wavelengths. It will also be appreciated by those skilled in the art that one or both of the frequency shifts $f_1$, $f_2$ may be the result of Zeeman splitting or like phenomena characteristic of the laser sources themselves.

In a next step, beams 11 and 12 are combined into a test beam 13 by an optical element 9, which is preferably a non-polarizing beam splitter. In a further step, test beam 13 propagates to an interferometer 60, comprised of optical means for a introducing a phase shift $\phi_1$ between the polarization components x and y of beam 13 corresponding to wavelength $\lambda_1$ and a phase shift $\phi_2$ between the polarization components x and y of beam 13 corresponding to wavelength $\lambda_2$. The magnitude of phase shifts $\phi_1$, $\phi_2$ are related to the physical length L of measurement path 66 according to the formulae $$\phi_j = Lk_j n_j + \zeta_j, \text{ for } j=1,2, \qquad (2.)$$

where the wavenumbers $k_j$ are given by $$k_j = 2\pi/\lambda_j \qquad (3.)$$

and the indices of refraction $n_j$ of the gas in measurement path 66 correspond to wavelengths $\lambda_j$. The phase offsets $\zeta_j$ comprise all contributions to the phase shifts $\phi_j$ that are not related to the measurement path 66.

As shown and preferred in FIG. 1, interferometer 60 is comprised of a reference mirror 65, a quarter-wave plate 21, a quarter-wave plate 22, a polarizing beam splitter 23 and object 67 connected to a motion stage 68, or the like, by which object 67 may be moved to alter measurement path 66. This configuration is known in the art as a polarized Michelson interferometer, and is shown as a simple illustration. An angle-compensating interferometer or similar device such as is described in an article entitled "Differential interferometer arrangements for distance and angle measurements: Principles, advantages and applications." by C. Zanoni (VDI Berichte Nr. 749, p.93, 1989), is preferably incorporated into the apparatus of the invention when working with stages commonly encountered in the microlithographic fabrication of integrated circuits. Other forms of interferometer known in the art as described in the above-cited article "Differential interferometer arrangements for distance and angle measurements: Principles, advantages and applications." by C. Zanoni (VDI Berichte Nr. 749, p.93, 1989), may be incorporated into the apparatus of FIG. 1 without significantly departing from the spirit and scope of the present invention.

After passing through interferometer 60, test beam 13 becomes a phase-shifted beam 15, which passes through a polarizer 44 preferably oriented so as to mix polarization components x and y of beam 15. A conventional dichroic beam splitter 80 preferably separates those portions of beam 15 corresponding to wavelengths $\lambda_1$ and $\lambda_2$ into two beams 16, 17 respectively. Beams 16, 17 then impinge upon a photodetectors 45, 46 respectively resulting in two heterodyne interference signals $s_1$, $s_2$ corresponding to the two wavelengths $\lambda_1$, $\lambda_2$ and having the form $$s_j = \cos[\alpha_j(t)], \text{ for } j=1,2, \qquad (4.)$$

where the time-dependent arguments $\alpha_1(t)$, $\alpha_2(t)$ of heterodyne interference signals $s_1$, $s_2$ are given by $$\alpha_j(t) = 2\pi f_j t + \phi_j \qquad (5.)$$

and the signal amplitude has been normalized to one and any constant offset values have been filtered out by conventional electronic pre-processing means (not shown). Heterodyne interference signals $s_1$, $s_2$ are transmitted to electronic processing means 98 for analysis.

Figure 3:
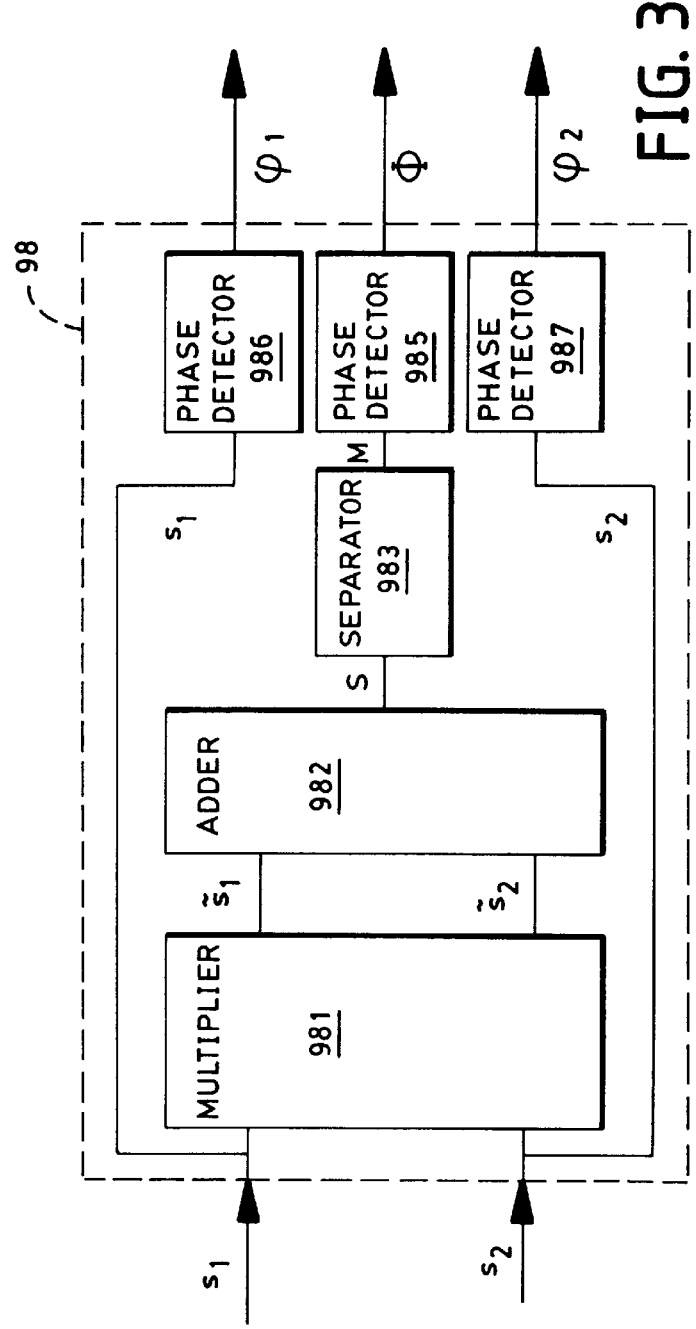
FIG. 3 is a drawing showing a block diagram of the processing electronics employed in the present invention.

Referring now to FIG. 3, electronic processing means 98 preferably comprises means 981 for electronically multiplying time-dependent arguments $\alpha_1(t)$, $\alpha_2(t)$ of heterodyne interference signals $s_1$, $s_2$ by coefficients $p_1$, $p_2$, respectively, so as to create two modified heterodyne signals $\tilde{s}_1$, $\tilde{s}_2$ having the form $$\tilde{s}_j = \cos[p_j \alpha_j(t)], \text{ for } j=1,2. \qquad (6.)$$

The multiplication may be achieved by any one of the conventional frequency multiplying techniques commonly known in the art, such as signal squaring followed by electronic filtering. It will be understood by those skilled in the art that such electronic multiplying techniques may introduce offsets and modifications in signal strength that may be neglected in the present, simplified description of the analysis technique of the present invention. It is noteworthy that the coefficients $p_1$, $p_2$ are preferably identical to the like-denoted coefficients $p_1$, $p_2$ used to define the approximate harmonic relationship in Eq.(1).

Referring again to FIG. 3, electronic processing means 98 preferably comprises means 982 for electronically adding two modified heterodyne signals $\tilde{s}_1$, $\tilde{s}_2$ together to create a superheterodyne signal S having the mathematical form $$S = \tilde{s}_1 + \tilde{s}_2 \quad (7.)$$

which may be rewritten as $$S = 2MC \quad (8.)$$

where $$C = \cos(2\pi vt + \theta) \quad (9.)$$

$$M = \cos(2\pi Ft + \Phi) \quad (10.)$$

and $$v = \tfrac{1}{2}(p_1 f_1 + p_2 f_2) \quad (11.)$$

$$\theta = \tfrac{1}{2}(p_1 \phi_1 + p_2 \phi_2)$$

$$F = \tfrac{1}{2}(p_1 f_1 - p_2 f_2) \quad (12.)$$

$$\Phi = \tfrac{1}{2}(p_1 \phi_1 - p_2 \phi_2).$$

Superheterodyne signal S is therefore a carrier signal C of frequency v modulated by an envelope signal M of frequency F. Those skilled in the art will appreciate that when modified heterodyne signals $\tilde{s}_1$, $\tilde{s}_2$ are of different amplitude, the resulting mathematical expression is more complicated, but nonetheless may be described in terms of a carrier signal modulated by an envelope signal. For simplicity in the present disclosure, it is assumed that modified heterodyne signals $\tilde{s}_1$, $\tilde{s}_2$ have the same amplitude.

Referring once again to FIG. 3, electronic processing means 98 preferably comprises a means 983 to separate envelope signal M from carrier signal C, using rectification and filtering, signal squaring, or any of the like techniques for extracting an amplitude modulation and demodulating a carrier. Electronic processing means 98 further comprises a means 985 to determine the modulation phase $\Phi$ using conventional time-based phase detection or the like. Electronic processing means 98 additionally comprises a means 986 and a means 987 to determine the phases $\phi_1$ and $\phi_2$, respectively.

In a next step, electronic processing means 98 transmits to a computer 99, in either digital or analog format, the values of modulation phase $\Phi$ and phase shifts $\phi_1$, $\phi_2$. Computer 99 calculates the carrier phase $\theta$ and calculates the refractive index using the formula $$n_1 = 1 + \frac{A}{L}(Kv - \chi\Phi - Q), \quad (13.)$$

where $$A = \frac{2\Gamma}{(\chi^2 - K^2)}, \quad (14.)$$

$$K = \frac{1}{2}(p_1 k_1 - p_2 k_2) \quad (15.)$$

$$\chi = \frac{1}{2}(p_1 k_1 + p_2 k_2) \quad (16.)$$

$$\Gamma = \frac{n_1 - 1}{n_2 - n_1} \quad (17.)$$

Constant $\Gamma$, defined above, is a measure of the dispersion of the refractive index of air. For example, if $\lambda_1 = 0.63\ \mu m$ and $\lambda_2 = 0.33\ \mu m$, then $\Gamma = 24$. The offset factor Q is defined as $$Q = K\xi - \chi Z, \quad (18.)$$

where $$\xi = \tfrac{1}{2}(p_1 \zeta_1 + p_2 \zeta_2) \quad (19.)$$

$$Z = \tfrac{1}{2}(i\ p_1 \zeta_1 - p_2 \zeta_2). \quad (20.)$$

For the presently-preferred embodiment of the invention, Q is considered a constant, or is monitored by purely electronic means (not shown).

The quantities K and $\chi$ introduced in Eqs. (15, 16) respectively will be referred to as the vacuum superheterodyne wavenumber and the vacuum carrier wavenumber, respectively. This terminology follows logically from the following two phase equations, which are valid when $n_1 = n_2 = 1$:

$$\theta = \chi L + \xi \quad (21.)$$

$$\Phi = KL + Z \quad (22.)$$

For the same reason, the quantities $\xi$ and Z introduced in Eqs. (19, 20) will be referred to as the vacuum carrier phase offset and the vacuum superheterodyne phase offset, respectively.

In a final step, for those applications related to distance measuring interferometry, the calculated value of refractive index $n_1$ together with the phase shift $\phi_1$ may be used to determine the distance L independent of fluctuations in refractive index $n_1$, using the formula $$L = \frac{\phi_1 - \zeta_1}{k_1 n_1} \quad (23.)$$

It would also be obvious to someone skilled in the art to perform similar calculations with respect to $n_2$ in place of or in addition to $n_1$.

A preferred embodiment of the present invention having been disclosed in the previous paragraphs, the underlying advantages of the present invention will be made more clear by the following discussion. It is evident from the calculation of the refractive index $n_1$ provided by the above equation that the required accuracies of the carrier phase $\theta$ and the superheterodyne phase $\Phi$ are related to the values of the carrier wavenumber $\chi$ and the superheterodyne wavenumber K. Since the frequency F of the modulation signal M can be very much smaller than the frequency v of carrier signal C, and since it is generally easier to calculate the phase with high resolution of an electronic signal of lower frequency, it is generally most advantageous to rely on a high-accuracy measurement of the superheterodyne modulation phase $\Phi$. This is readily achieved in the apparatus of the present invention when the wavelengths $\lambda_1$, $\lambda_2$ are approximately harmonically related, as shown above in the first equation. For the limit case where $\lambda_1$, $\lambda_2$ are integer multiples of each other, i.e. for the limit case where $$p_1\lambda_2 \approx p_2\lambda_1 \text{ for } p_1, p_2=1,2,3,\ldots, p_1 \neq p_2 \quad (24.)$$

the vacuum superheterodyne wavenumber K is equal to zero and the refractive index calculation does not involve the carrier phase θ at all as illustrated by the following expression:

$$n_1 = 1 + \frac{A}{L}(\chi\Phi - Z) \text{ for } K = 0. \quad (25.)$$

Further, for the case where K=0, the superheterodyne modulation phase Φ is also only weakly dependent upon the distance L, relative to the very strong dependence of the carrier phase θ and of the phase shifts $\phi_1$, $\phi_2$. This greatly improves the phase detection accuracy for moving objects, such as are commonly encountered in microlithography equipment.

An important consideration for interferometry in general and for dispersion techniques in particular is source wavelength instability. The apparatus of the present invention provides a convenient way of compensating for source wavelength instability as follows. By mathematical manipulation of Eq. (13), it is possible to show that an error $\delta n_1$ in refractive index attributable to source wavelength instability is given by $$\delta n_1 \approx \chi A \delta K, \quad (26.)$$

where δK is the instability in the vacuum superheterodyne wavenumber K. This formula shows that the magnitude of the error is substantially independent of the object distance L, and of all other variables such as the phase shifts $\phi_1$, $\phi_2$ that depend directly on the object distance L. It is therefore possible to compensate for the effects of wavelength stability by measuring the index of refraction along a monitor path that is entirely free of real fluctuations in index. Any measured variations are the result of wavelength instability.

Figure 4:
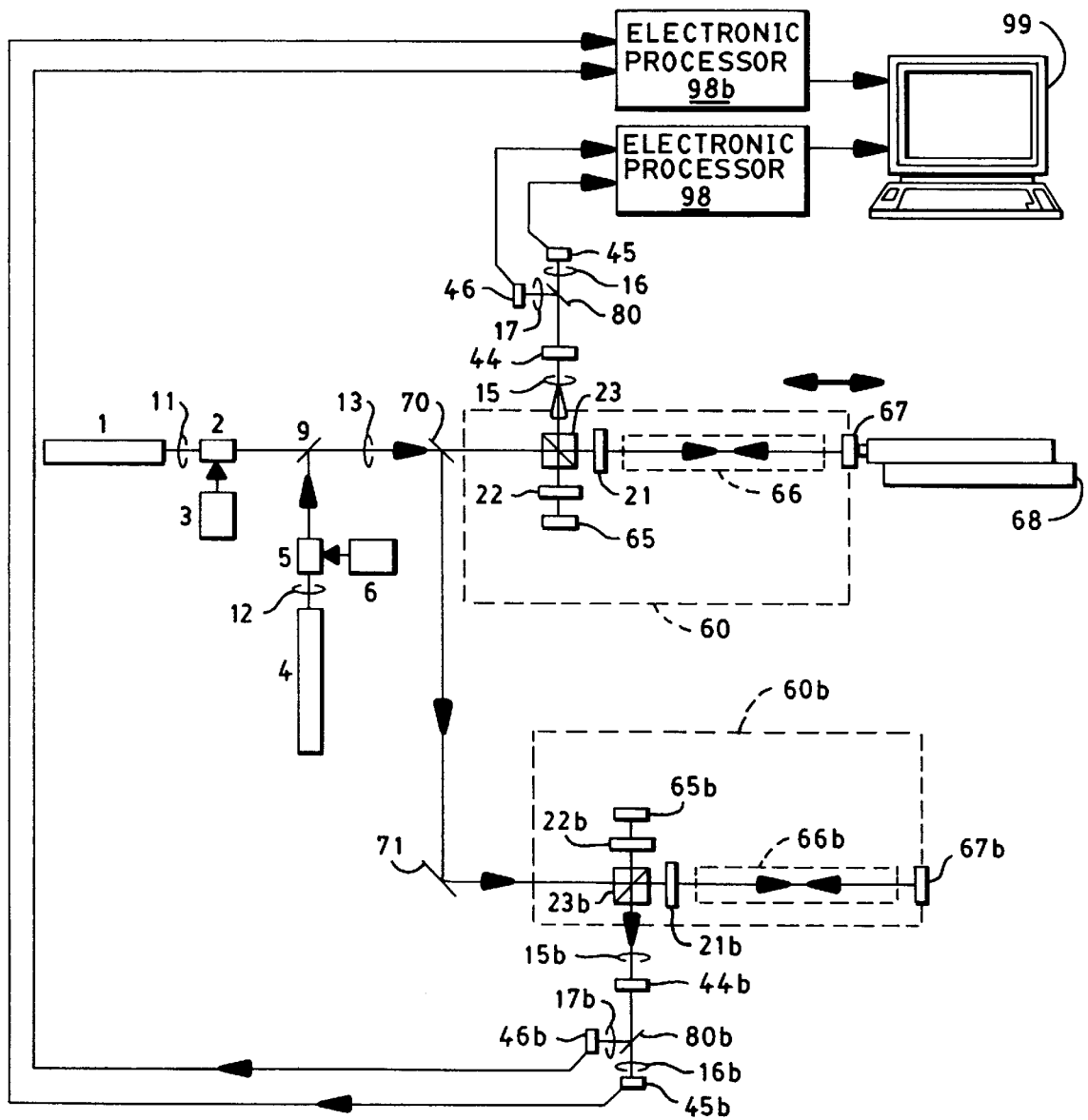
FIG. 4 is a drawing showing an alternative embodiment of the present invention.

Referring now to FIG. 4, there is shown an alternative embodiment of the present invention in which a monitor system 60b has been added to the embodiment of FIG. 1 for the purpose of compensating for an error $\delta n_1$ in refractive index measurement attributable to source wavelength instability. A beam splitter 70 and a mirror 71 reflect a portion of beam 13 towards monitor system 60b. Monitor system 60b comprises a number of elements performing analogous operations as interferometer 60, with elements performing like operations as like denoted elements as interferometer 60, apart from the suffix "b" when referring to elements of monitor system 60b. A monitor electronic processing system 98b similarly performs like operations as electronic processing system 98. The difference between interferometer 60 and monitor system 60b is that monitor path 66b of monitor system 60b is preferably a fixed length, with a carefully controlled refractive index, such as may be achieved by enclosing monitor path 66b and controlling the temperature and pressure of the enclosed volume. In that the refractive index along monitor path 66b is substantially constant, any measured variations $\delta n_M$ in the monitor system are attributable to source wavelength instability. For this alternative embodiment of the present invention, computer 99 preferably calculates refractive index $n_1$ according to the formula $$n_1 = 1 + \frac{A}{L}(K\upsilon - \chi\Phi - Q) - \delta n_M, \quad (27.)$$

This preferred compensation technique of the present invention greatly reduces the wavelength stability requirements for the source. It is particularly noteworthy that the present invention does not require absolute wavelength stability, and a monitor path 66b need not have an extraordinarily stable physical length L.

The advantages of the present invention are: (1) the present invention provides accurate measurement of and compensation for fluctuations in the refractive index of air, such as is useful for distance measuring interferometry; (2) the present invention is compatible with the rapid stage motion common to modern microlithography equipment; (3) the present invention optionally comprises easily-incorporated monitor means and method to substantially reduce source stability requirements; and (4) the apparatus of the present invention is substantially less complicated and expensive relative to comparable prior art.

It will be appreciated by those skilled in the art that alternative data processing may be considered without departing from the spirit and scope of the present invention, such as for example, it may prove useful to multiply modified heterodyne signals $\tilde{s}_1$, $\tilde{s}_2$ together rather than adding them, as was proposed above resulting in the expression:

$$S' = \tilde{s}_1 \tilde{s}_2 \quad (28.)$$

Alternative signal S' may be generated by selecting the appropriate term in the binomial expansion of $(s_1+s_2)^{p+q}$ through the use of phase sensitive detection. Alternative signal S' would then be comprised of the sum, rather than the product, of two signals having frequencies F and ν. Such a processing technique would prove advantageous for example if it were found useful to replace detectors 45, 46 and dichroic beam splitter 80 in FIG. 1 with a single detector.

It will further be appreciated by those skilled in the art that alternative additional optical elements and electronic processing steps may be incorporated into one of the disclosed embodiments of the apparatus of the present invention. For example, additional detectors and associated elements may be added to the embodiments to measure and compensate for the various phase offsets encountered in the data processing. These and other obvious modifications may be introduced without departing from the spirit and scope of the present invention.

What is claimed is:

1. An apparatus for measuring fluctuations in the refractive index of a gas in a measurement path comprising:

a source of at least two light beams having different wavelengths and a substantially harmonic relationship, said light beams each having orthogonal polarization states;

means for introducing a frequency difference between said orthogonal polarization states of each of said light beams;

means for aligning said light beams into a single substantially collinear light beam along said measurement path;

means for producing phase shifted beams having phase shift magnitudes proportional to a product of the physical length of said measurement path and said refractive index of said gas in said measurement path;

means for mixing said polarization components of each of said phase shifted beams for producing at least two mixed output beams;

means for producing heterodyne electrical signals from the intensities of said at least two mixed output beams which comprise oscillations at heterodyne frequencies related to the frequency differences between said polarization states of said light beams and comprising heterodyne phases which are substantially inversely related in accordance with said harmonic relationship between said different wavelengths except for differences due to said refractive index of said gas in said measurement path;

means for generating at least two modified heterodyne signals from said at least two heterodyne electrical signals which comprise modified heterodyne frequencies and modified heterodyne phases harmonically related to said heterodyne phases in accordance with the ratio of said different wavelengths;

means for adding at least one preselected pair from said at least two of said modified heterodyne electrical signals for producing one superheterodyne electrical signal comprising a superheterodyne modulation frequency substantially equal to half the difference of said preselected pair of said modified heterodyne frequencies and a superheterodyne modulation phase substantially equal to half the difference between said heterodyne phases of said preselected pair of said modified heterodyne electrical signals; and means for analyzing said superheterodyne modulation phase for determining said fluctuations in said refractive index over said measurement path.

2. An apparatus in accordance with claim 1 wherein said frequency difference of each of said light beams differs from that of every other of said light beams.

3. An apparatus in accordance with claim 1 wherein said means for aligning said light beams comprises optical means for aligning all of said light beams into said single light beam.

4. An apparatus in accordance with claim 1 wherein said means for producing said phase shifted beams comprises means for introducing phase shifts between the polarization states of each of said light beams.

5. An apparatus in accordance with claim 4 wherein said means for producing said phase shifted beams comprises optical means.

6. An apparatus in accordance with claim 1 wherein said means for producing said phase shifted beams comprises optical means.

7. An apparatus in accordance with claim 1 wherein said refractive index of said gas is a function of wavelength and comprises a different refractive index for each of said phase shifted beams.

8. An apparatus in accordance with claim 1 wherein said means for mixing said polarization components comprises a polarizer.

9. An apparatus in accordance with claim 1 wherein said means for producing said heterodyne electrical signals comprises photoelectric detection means.

10. An apparatus in accordance with claim 1 wherein said means for adding at least one preselected pair from said at least two of said modified heterodyne electrical signals comprises means for adding any two of said modified heterodyne electrical signals for producing said one superheterodyne electrical signal comprising an amplitude modulated carrier having said superheterodyne modulation frequency.

11. An apparatus in accordance with claim 1 wherein said source comprises a source of coherent radiation.

12. An apparatus in accordance with claim 11 wherein said source comprises a laser.

13. An apparatus in accordance with claim 1 wherein said measurement path comprises a measurement path in an interferometer.

14. An apparatus in accordance with claim 1 wherein said gas is air.

15. An apparatus in accordance with claim 1 wherein said means for generating said modified heterodyne signals comprises electronic means.

16. An apparatus in accordance with claim 1 further comprising means for compensating for errors in said superheterodyne modulation phase produced by fluctuations in the wavelengths of said source.

17. An apparatus in accordance with claim 16 wherein said compensating means comprises interferometer means having a measurement path comprised of a monitor path of fixed length and a gas having a controlled refractive index.

18. An apparatus in accordance with claim 17 wherein said compensation means further comprises means for producing monitor heterodyne signals, said generating means further comprising means for producing modified monitor heterodyne signals from said monitor heterodyne signals.

19. An apparatus in accordance with claim 18 wherein said means for producing said modified monitor heterodyne signals comprises electronic means.

20. An apparatus in accordance with claim 18 wherein said compensation means further comprises means for adding any two of said modified monitor heterodyne electrical signals for producing said at least one monitor superheterodyne electrical signal, said monitor superheterodyne signal comprising an amplitude modulated carrier having monitor superheterodyne modulation frequency.

21. The apparatus of claim 13 further including means for mounting an object at least at one end of said measurement path for selective movement with respect thereto such that said measurement path changes in accordance with changes in the position of said object and means for analyzing said superheterodyne modulation signal to measure the position of said object substantially independently of fluctuations of said refractive index of said gas as said object is moved.

22. A method for measuring fluctuations in the refractive index of a gas in a measurement path, said method comprising the steps of:

providing at least two light beams having different wavelengths and a substantially harmonic relationship, said light beams each having orthogonal polarization states;

introducing a frequency difference between said orthogonal polarization states of each of said light beams;

aligning said light beams into a single substantially collinear light beam along said measurement path;

producing phase shifted beams having phase shift magnitudes proportional to a product of the physical length of said measurement path and said refractive index of said gas in said measurement path;

mixing said polarization components of each of said phase shifted beams for producing at least two mixed output beams;

producing heterodyne electrical signals from the intensities of said at least two mixed output beams which comprise oscillations at heterodyne frequencies related to the frequency differences between said polarization states of said light beams and comprising heterodyne phases which are substantially inversely related in accordance with said harmonic relationship between said different wavelengths except for differences due to said refractive index of said gas in said measurement path;

generating at least two modified heterodyne signals from said at least two heterodyne electrical signals which comprise modified heterodyne frequencies and modified heterodyne phases harmonically related to said heterodyne phases in accordance with the ratio of said different wavelengths;

adding at least one preselected pair from said at least two of said modified heterodyne electrical signals for producing one superheterodyne electrical signal comprising a superheterodyne modulation frequency substantially equal to half the difference of said preselected pair of said modified heterodyne frequencies and a superheterodyne modulation phase substantially equal to half the difference between said heterodyne phases of said preselected pair of said modified heterodyne electrical signals; and analyzing said superheterodyne modulation phase for determining said fluctuations in said refractive index over said measurement path.

23. The method of claim 22 wherein said frequency difference of each of said light beams differs from that of every other of said light beams.

24. A method in accordance with claim 22 wherein said gas is air.

25. A method in accordance with claim 22 wherein said measurement path comprises a measurement path in an interferometer having a stage movable along said measurement path, said superheterodyne modulation phase providing step comprising the step of providing said superheterodyne modulation phase substantially insensitive to stage motions in said measurement path.

26. A method in accordance with claim 22 further comprising the step of determining a distance L along said measurement path independent of said fluctuations in said refractive index n.

27. A method in accordance with claim 22 wherein said distance determining step further comprises the step of determining said distance L in accordance with the expression $$L = \frac{\phi_1 - \zeta_1}{k_1 n_1}$$

where $\phi_1$ equals the magnitude of the phase shift, $k_1$ equals the wavenumber of the phase shift, n equals the refractive index and $\zeta_1$ equals the phase offset, the phase offset comprising all contributions to the phase shift $\phi_1$ that are not related to the measurement path.

28. A method in accordance with claim 22 wherein the step of providing said source light beams comprises the step of providing source light beams having orthogonal polarization states having a frequency difference between said orthogonal polarization states, and the step of providing modified heterodyne phase shifts based on said provided source wavelengths comprises the steps of producing heterodyne electrical signals which comprise oscillations at heterodyne frequencies related to frequency differences between polarization states of said source light beams, and generating modified heterodyne signals from said heterodyne electrical signals which comprise said modified heterodyne phase shifts.

29. A method in accordance with claim 28 wherein said generating step comprises the step of electronically generating said modified heterodyne signals, said method further comprising the step of electronically adding said modified heterodyne signals for producing a superheterodyne signal comprising said superheterodyne modulation phase.

30. A method in accordance with claim 22 further comprising the step of compensating for errors in said superheterodyne modulation phase produced by fluctuations in the source wavelengths.

* * * * *